(12) United States Patent
Ritter

(10) Patent No.: US 7,264,397 B2
(45) Date of Patent: Sep. 4, 2007

(54) METHOD AND X-RAY SYSTEM FOR DETERMINATION OF POSITION OF AN X-RAY SOURCE RELATIVE TO AN X-RAY IMAGE DETECTOR

(75) Inventor: Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/498,652

(22) Filed: Aug. 2, 2006

(65) Prior Publication Data

US 2007/0030959 A1 Feb. 8, 2007

(30) Foreign Application Priority Data

Aug. 2, 2005 (DE) .................. 10 2005 036 285

(51) Int. Cl.
*A61B 6/08* (2006.01)

(52) U.S. Cl. ........................ 378/205; 378/207

(58) Field of Classification Search ................ 378/162, 378/163, 164, 205, 207; 382/294
See application file for complete search history.

(56) References Cited

U.S. PATENT DOCUMENTS 6,671,349 B1 * 12/2003 Griffith ...................... 378/163

OTHER PUBLICATIONS

"Feature-Based Object Recognition and Localization in 3D-Space Using a Single Video Image," Häusler et al, Computer Vision and Image Understanding, vol. 73, No. 1 (Jan. 1999) pp. 64-81.
"Enhanced 3-D-Reconstruction Algorithm for C-Arm Systems Suitable for Interventional Procedures," Wiesent et al, IEEE Trans. On Medical Imaging, vol. 19, No. 5 (May 2000) pp. 391-403.
"Portable Hard X-ray Source for Non-Destructive Testing and Medical Imaging," Boyer et al, Review of Scientific Instruments, vol. 69, No. 6 (Jun. 1998) pp. 2524-2530.

* cited by examiner

*Primary Examiner*—Courtney Thomas
(74) *Attorney, Agent, or Firm*—Schiff Hardin LLP

(57) ABSTRACT

In a method and x-ray system for determination of the relative position of an x-ray source relative to an x-ray image detector, a reference structure in a known position relative to the x-ray source is introduced into the beam path between the x-ray source and the x-ray image detector. The x-ray image detector acquires an x-ray image with the map of the reference structure. The position of the map of the reference structure in the x-ray image is determined by a computer and the position of the reference structure relative to the x-ray image detector is determined therefrom. The position of the x-ray source relative to the x-ray image detector is determined from this relative position of the reference structure to the x-ray image detector and from the position of the reference structure to the x-ray source.

20 Claims, 1 Drawing Sheet

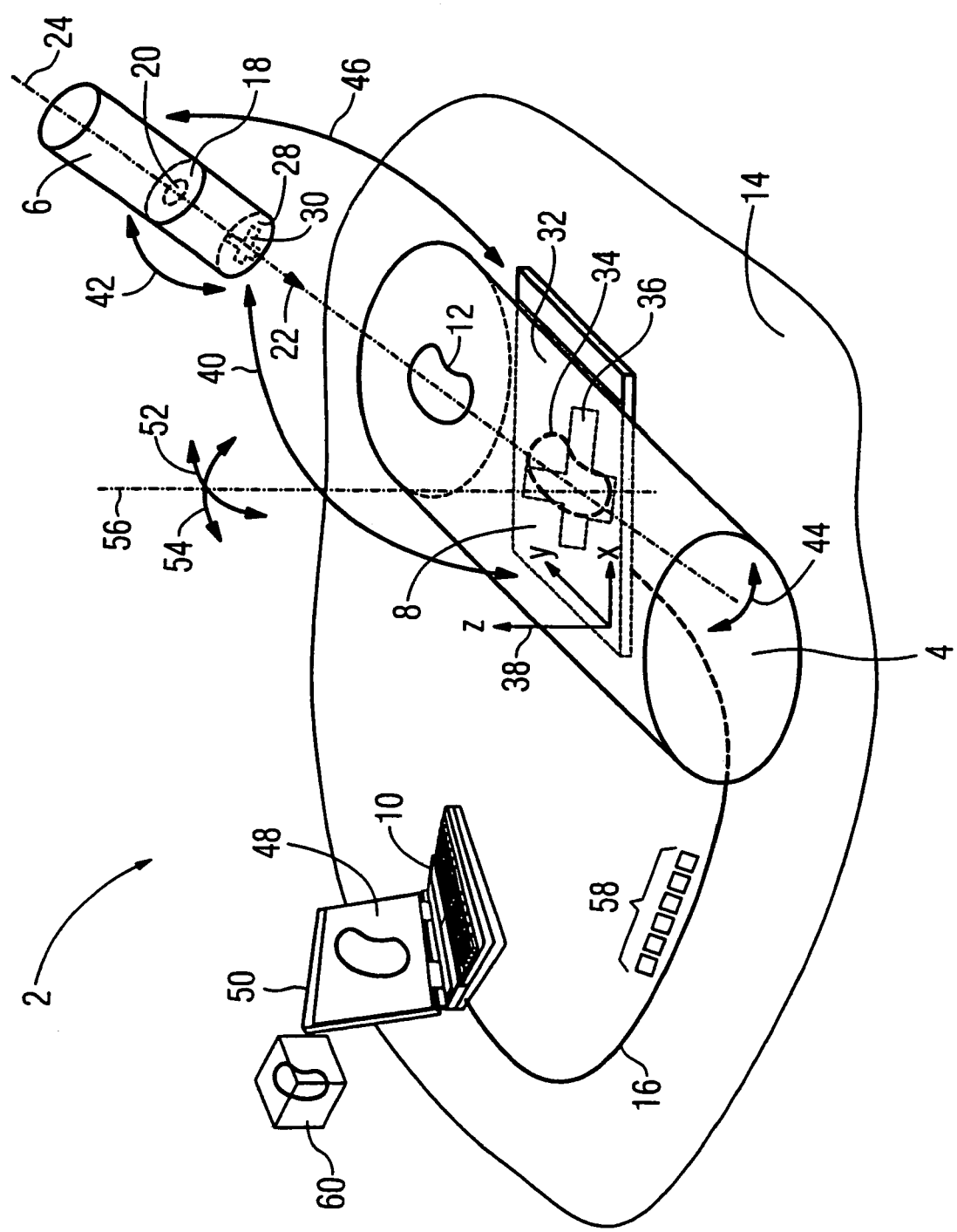

METHOD AND X-RAY SYSTEM FOR DETERMINATION OF POSITION OF AN X-RAY SOURCE RELATIVE TO AN X-RAY IMAGE DETECTOR

BACKGROUND OF THE INVENTION

Field of the Invention

The present invention concerns a method for determination of the position of an x-ray source relative to an x-ray image detector and a corresponding x-ray system.

X-ray systems generally have an x-ray source and an x-ray image detector, for example in the form of an x-ray image intensifier or a planar image detector. The knowledge of the precise geometric positions of x-ray source and x-ray image detector, relative to one another or relative to the subject to be exposed, is increasingly important for the evaluation of the x-ray images acquired with such an x-ray system. This is particularly true when multiple images of a subject are acquired with the x-ray system from various viewing (projection) directions in order to subsequently reconstruct a 3D volume of the subject.

Moreover, portable, battery-operated x-ray radiators and portable, battery-operated planar image detectors have become known in x-ray technology. Both together are used today as a portable x-ray system (mostly in combination with a laptop for immediate viewing or evaluation of the acquired x-ray images) primarily in emergency care of immobile persons in the field or in crisis areas with mobile ambulances. Veterinary medicine also offers a broad application field for such x-ray systems.

It has also become desirable to also generate reconstructed 3D reconstruction volumes of x-rayed subjects with such a mobile system. As already mentioned, the precise knowledge of the projection directions in which the x-ray exposures of the subject are made is decisive for the quality of the 3D reconstruction. Precise knowledge of the relative position of x-ray source and x-ray detector for each x-ray exposure is thus necessary.

In some portable x-ray image detectors, an "autosense" mode is available meaning that the acquisition of an x-ray image is automaUcally triggered given incident x-ray radiation. Cabling between the x-ray source the x-ray image detector thus is omitted in such a portable system. Only the laptop is normally connected with the x-ray image detector via a data line. This advantage of the simplicity of the system should be retained in the generation of 3D image data of a subject with such system.

Therefore, in such a system the use of an external navigation system is undesirable, since optical and magnetic navigation systems (for example with localizable radiofrequency transponders, mechanical systems or other such equipment) are technically complicated, voluminous, cumbersome and very costly. The use of such navigation systems in combination with the extremely flexible and mobile x-ray system that is nearly without cabling is complicated and counterproductive.

Therefore, only stationary x-ray systems (known as angio systems) and mobile C-arms (known as OP systems) have been known for generation of 3D image data. In contrast to the portable system described above, the term "mobile" means that such a C-arm unit can be moved within a clinic area, for example within an operating theater or between various rooms. A truly mobile (portable) use in the open field as explained above is not reasonable with these known mobile C-arms, which is why these are likewise classified as stationary in the sense of the present application.

The determination of the relative position of x-ray source and the x-ray image detector, or their position relative to the subject to be exposed is established once in system-specific projection matrices in the stationary systems using items known as calibration phantoms. The reproducible mechanical deformations (warpings) etc. of such systems are thereby mapped or corrected. For the most part, such projection matrices are thereby specified for an angulation range of ±30°.

SUMMARY OF THE INVENTION

An object of the present invention is to provide an improved method for determination of the position of an x-ray source relative to an x-ray image detector and a corresponding x-ray system.

The above object is achieved in accordance with the invention by a method for determination of the position of an x-ray source relative to an x-ray image detector, wherein a reference structure in a known position relative to the x-ray source is introduced into the beam path between x-ray source and x-ray image detector, and the x-ray image detector acquires an x-ray image of the reference structure, and the position of the map of the reference structure in the x-ray image is determined. The relative position of the reference structure relative to the x-ray image detector is determined therefrom and the position of the x-ray source to the x-ray image detector is determined from this position of the reference structure relative to the x-ray image detector and from the relative position of the reference structure relative to the x-ray source.

In contrast to the external solutions described above, the inventive method represents an intrinsic way to determine the positions of the x-ray source and the x-ray image detector. It is intrinsic because the position determination or position detection is executed solely from the x-ray image without additional navigation or positioning devices. Only the reference structure is necessary.

The determination of the position of the map of the reference structure in the x-ray image forms the core of the position determination. With suitable methods of pattern recognition or image processing, the determination or calculation of the geometric position of the reference structure relative to the image plane of the x-ray image can be calculated or determined from the actual geometric shape or the dimensions of the corresponding reference structure, and the shape or the dimensions of the map of the reference structure in the x-ray image. The six degrees of freedom of this position, namely both the coordinates and the rotation angles of the reference structure relative to the image plane of the x-ray image, thus can be determined.

An example of a suitable method for localization or position determination of a mapped subject (in the present case the reference structure in an image, i.e. the x-ray image) is known from Häusler, G. et al., "Feature-Based Object Recognition and Localization in 3D-Space, Using a Single Video Image", Computer Vision and Image Understanding, volume. 73, Nr. 1, January 1999, www.idealibrary.com.

Since the position of the image plane relative to or in the x-ray image detector is in turn "known" to the x-ray image detector, and the relative position of reference structure and x-ray source is "known" to the x-ray source, the determination of the relative position of x-ray source and x-ray image detector is enabled.

The reference structure can be any structure or arrangement or shape that, due to two-dimensional mapping thereof in the imaging system, allows an unambiguous three-dimensional position determination from this map. Asymmetrical figures or shapes, for example based on cruciate or circular shapes, are particularly suitable for this purpose. The circular shape is suitable, for example for an ellipse search in the x-ray image; the cruciate shape is suitable for an identification in the Fourier domain of the x-ray image.

The reference structure naturally must be provided so that it can be mapped on the x-ray image by x-ray radiation.

Since a determination of the relative positions of the x-ray source and x-ray image detector is in principle possible from every acquired x-ray image using the inventive method, a calibration segment, as in known x-ray methods, is unnecessary in stationary x-ray systems.

The requirement for this is merely that the mapping of the reference structure in the x-ray image does not disturb, or only insignificantly disturbs, the other image information, and vice versa. Naturally, for reproducible relative positions that the x-ray source and the x-ray image detector can adopt it is also possible to implement the inventive procedure in a first pass in a geometry calibration, which provides the relative position of the x-ray image detector and the x-ray source. Subsequently a diagnostic x-ray exposure (for example) of a subject of interest is acquired for purely diagnostic purposes, without a reference structure in the x-ray path.

The reference structure can be mounted in front of the exit aperture of the x-ray source as a structured x-ray mask. An x-ray mask can easily be mounted at this point permanently or so that it can be removed. Due to the (normally advantageous) design of the housing of the x-ray source at the exit aperture, the x-ray mask can easily be mechanically placed there exactly, in a securable manner, in a precisely reproducible position. Due to the structuring of the x-ray mask, the reference structure can be mounted in a simple manner thereon, such as by gluing or mechanical attachment.

The reference structure can be formed on the x-ray mask by locally-different plate thicknesses of the x-ray mask. Suitable x-ray masks can be manufactured particularly simply. The reference structure on the x-ray mask cannot be lost and the x-ray mask then forms a single component together with the reference structure.

The reference structure can be designed in an arbitrary manner as long as the aforementioned conditions are satisfied. For example, the reference structure can be formed as four asymmetrically mounted, radiologically-detectable points in a pattern on the aforementioned x-ray mask.

An asymmetrical cross with arms of different widths also can be used as the reference structure. As already mentioned, the map of a cross structure in an x-ray image can be particularly easily located by Fourier transformation of the x-ray image and searching in the Fourier space.

The x-ray attenuation caused by the reference structure in the beam path between the x-ray source and the x-ray image detector can be determined, and a first x-ray image of a subject together with the reference structure can be acquired, and an artificial second x-ray image corresponding to the x-ray image without reference structure in the beam path can be determined from the first x-ray image taking the x-ray attenuation into account.

In other words, in this version of the method the mapping of the reference structure in the x-ray image is eliminated after the acquisition thereof. The variation of the mapping of the subject in the x-ray image caused by the influence of the reference structure is known since this was determined in advance. As a result, a second artificial x-ray image is created that corresponds to an x-ray image of the subject which would have been acquired with a reference structure in the beam path. Nevertheless, the actual acquired x-ray image allows the position determination of x-ray source and x-ray image detector simultaneously with the acquisition of the subject.

A mobile x-ray source can be used as the x-ray source and a mobile x-ray image detector can be used as the x-ray image detector. The inventive method is particularly advantageous for the aforementioned portable, battery-operated x-ray system components, for example in connection with a laptop. A relative position determination of the individual components relative to one another occurs without elaborate, expensive, voluminous auxiliary means with each x-ray exposure that is acquired with the reference structure. All determinations or calculations can be implemented automatically, for example in the form of a computer program running on the laptop.

With the inventive method, a series of x-ray images of a subject also can be acquired at various viewing directions caused by various relative positions of the x-ray source and the x-ray image detector relative to one another. The positions of the x-ray source and the x-ray image detector relative to one another can be determined, and a 3D reconstruction volume of the subject can be determined from the series of x-ray images using the determined relative positions.

The generation of 3D image data without elaborate additional auxiliary means is thus also possible with a truly mobile (i.e. portable), battery-operated x-ray system as described above. It is only necessary that the various viewing directions from which the subject is mapped in the various x-ray exposures can be determined, since these are necessary for 3D reconstruction. Since, according to the invention, the viewing directions can be unambiguously associated with the various relative positions of the x-ray source and the x-ray image detector, the viewing direction of every x-ray image can be determined from the relative position determination of the x-ray source and the x-ray image detector. In other words, it is a requirement for 3D reconstruction that the different viewing directions or geometric relationships of the exposures that are necessary for the 3D reconstruction are determined from the relative positions of the x-ray image detector and the x-ray source with regard to the subject.

This is particularly the case when the x-ray image detector can be fixed in a fixed relative position relative to the subject placed between it and the x-ray source, and the x-ray source is panned in a predetermined azimuthal and elevation angle range relative to the perpendicular (surface normal) of the x-ray image detector for acquisition of the series of x-ray images. Each position change between the x-ray source x-ray image detector follows from a change of the viewing direction from the x-ray source to the subject which is in turn reflected in the x-ray image. The aforementioned lack of ambiguity is thus provided. In practice, this can be simply achieved, for example, by a patient (as a subject to be mapped) resting on an x-ray image detector lying on the floor. The patient and the x-ray image detector are thus fixed relative to one another respectively to the floor. The x-ray source can then be panned over the patient and the x-ray image detector, relative to both of these, so the change of the relative position relative to the x-ray image detector directly correlates with the change of the viewing direction in the x-ray image.

The x-ray source and/or the x-ray image detector can be moved manually or hands-free (automatically). The manual panning, for example of the x-ray source relative to a stationary detector, is particularly suitable for the aforementioned field use of an x-ray system. In order to ensure at least approximately-reproducible manual panning movements of the x-ray source compared to completely automated panning, for example, a simple and light stand or the like can be used. This limits neither the weight nor the mobility, volume or the like of a complete mobile x-ray system, in contrast to the aforementioned navigation systems.

The object also is achieved by an x-ray system with an x-ray source and an x-ray image detector, and with a reference structure that can be introduced into the beam path between the x-ray source and the x-ray image detector in a known relative position relative to the x-ray source. An evaluation unit determines the position of the map of the reference structure in an x-ray image acquired of the x-ray image detector and determines therefrom the relative position of the reference structure relative to the x-ray image detector, and from this and from the known spatial position of the reference structure relative to the x-ray source, determines the relative position of the x-ray source relative to the image detector.

An x-ray system for execution of the inventive method is achieved by the evaluation unit. As mentioned above, such an evaluation unit can be, for example, a computer program running on a connected laptop.

The advantages of the x-ray system as well as its inventive developments have already been explained in connection with the inventive method.

DESCRIPTION OF THE DRAWINGS

The single FIGURE shows a mobile x-ray system for generation of 3D image data of a patient.

DESCRIPTION OF THE PREFERRED EMBODIMENTS

FIG. 1 shows a situation during the field usage of a mobile, battery-operated x-ray system 2 on a patient 4 to be irradiated. The shown patient 4 is ill and not capable of transport, thus immobile. The patient 4 is located in the field and must be examined or x-rayed there. The x-ray system 2 is therefore completely battery-operated and has a battery-operated x-ray source 6, a battery-operated planar detector 8 and a battery-operated laptop 10.

3D image data of the kidney 12 of the patient 4 are to be generated with the x-ray system 2. For this reason, the planar detector 8 is placed or inserted between the patient 4 lying on the ground 14 and the ground 14. The planar detector 8 is moreover connected with the laptop 10 via a data line 16.

On its front side 18, the x-ray source 6 has an exit aperture 20 through which the x-ray radiation (not shown) is radiated in the direction of the arrow 22 (i.e. in the direction of the central ray 24 of the x-ray system 2) toward the planar detector 8.

By means of a mounting 26, an x-ray mask 28 is attached on the x-ray source 6 in a fixed manner and at a known distance or at a known geometric position relative to the x-ray source 6. A reference structure 30 in the form of an irregular, asymmetric cross is in turn applied on the x-ray mask 28, effected by variations of its layer thickness.

A doctor (not shown) now manually holds the x-ray source 6 in the position shown in FIG. 1, whereby he or she targets the planar detector 8 or its center by visual judgment along the center ray 24. The doctor thus radiologically images the kidney 12 of the patient 4 on the planar detector 8. The doctor thereby roughly utilizes the assumed position of the kidney 12 in the patient 4. If the doctor discovers that he or she has focused on the desired region of the patient 4, the doctor initiates an x-ray shot at a trigger button (not shown) on the x-ray source 6, meaning that a specific dose of x-ray radiation is emitted along the central ray 24 to the planar detector 8.

The x-ray image 32 so generated in the planar detector 8 is symbolically mapped on the planar detector 8 in FIG. 1. The x-ray image 32 includes the image 34 of the kidney 12 and the image 36 of the reference structure 30.

The x-ray image 32 is transferred to the laptop 10 via the data line 16 and is evaluated there. The evaluation now occurs as follows.

An imaginary coordinate system 38 is attached to the planar detector 8 such that its x-y plane spans the imaging plane of the x-ray image 32 and its z-direction shows in the normal direction of the planar detector 8 (away from the ground 14 in FIG. 1). By the evaluation of the coordinates of the image 36 in the x-y plane of the coordinate system 38, the six degrees of freedom of the coordinates of the reference structure 30 (thus its three x-y-z coordinates and the three rotation angles around the corresponding axes) are themselves determined in the coordinate system 38. The relative position is symbolically shown by the double arrow 40 in FIG. 1.

Furthermore, as mentioned above the relative position of the reference structure 30 relative to the x-ray source 6 is known (indicated in FIG. 1 by the double arrow 42). Since, as mentioned and as shown in FIG. 1 by the double arrow 44, the position of the image 36 is moreover known in the coordinate system 38 attached to the planar image detector 8 (and thus relative to the planar image detector 8 itself), the relative position of x-ray source 6 and planar detector 8 (indicated by the arrow 46) is determined in the laptop 10 from these three relative positions.

Since an empty exposure of the reference structure 30 (as shown in FIG. 1 but without patient 4) was implemented in a previous calibration step (not shown), it is known how the reference structure 30 attenuates the x-ray radiation between the x-ray source 6 and the planar image detector 8. This information was stored in the laptop 10 as an attenuation factor in the calibration step. It is now used to multiply the x-ray image 32 with the inverse stored attenuation factor so that the image 36 of the reference structure 30 is cleared from the x-ray image 30 and a further artificial x-ray image 48 is thus generated which shows only the image 34 of the kidney 12. This x-ray image 48 is shown on the screen 50 of the laptop 10. It corresponds to an imaginary x-ray image of the patient 4 acquired without reference structure 30.

The doctor now manually pans the x-ray source 50 in the direction of the arrows 52 and 54, i.e. in a specific azimuthal and elevation angle range with regard to the surface normal 56 of the planar detector 8, whereby it is always endeavored to home in on the center of the planar detector 8 with the central ray 24. The doctor pans through the angle ranges (for example respectively +/−60°) according to visual judgment or experience.

By repeated triggering of x-ray exposures and the procedures as described above, a series 58 of x-ray images is thus created corresponding to the x-ray image 32, which series 58 is continuously transmitted via the data line 16 to the laptop 10 and is stored therein. A 3D reconstruction volume 60 of the patient 4 or the kidney 12 is calculated in the laptop 10 from the series 58 of x-ray images since the relative positions (indicated by the arrow 46) between x-ray source and planar detector 8 have already been respectively determined for the acquisition of each of the x-ray images of the series 58 according to the procedure described above.

Since the images 36 of the reference structure 30 have already been removed from the series 58 of x-ray images according to the procedure described above, these images 36 also do not lead to artifacts in the 3D reconstruction volume 60.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining a position of an x-ray source relative to an x-ray image detector in an x-ray imaging system, comprising the steps of:
   introducing a reference structure into a beam path of x-rays between an x-ray source and an x-ray image detector, at a known position relative to the x-ray source;
   acquiring an x-ray image with said x-ray image detector in which said reference structure is mapped;
   automatically electronically determining a position of the map of the reference structure in the x-ray image;
   automatically electronically determining a position of the reference structure relative to the x-ray image detector from the position of the map of the reference structure in the x-ray image;
   automatically electronically determining a position of the x-ray source relative to the x-ray image detector from the position of the reference structure relative to the x-ray image detector and the position of the reference structure relative to the x-ray source;
   irradiating an examination subject with x-rays emitted by said x-ray source and detecting attenuation data, representing attenuation of said x-rays by said examination subject, with said x-ray image detector, and generating an image of the examination subject using said attenuation data and the automatically electronically determined position of the x-ray source relative to the x-ray image detector.

2. A method as claimed in claim 1 wherein said x-ray source has a beam exit aperture, and wherein the step of introducing a reference structure into the beam path comprises attaching a structured x-ray mask in front of said exit aperture of said x-ray source.

3. A method as claimed in claim 2 comprising forming said structured x-ray mask from a plurality of locally-differing plate thicknesses.

4. A method as claimed in claim 1 comprising employing an asymmetric cross having cross-arms of respectively different widths as said reference structure.

5. A method as claimed in claim 1 comprising:
   determining an x-ray attenuation caused by said reference structure in said beam path between said x-ray source and said x-ray image detector;
   acquiring a first x-ray image of an examination subject together with said reference structure by irradiating said examination subject and said reference structure with x-rays in said beam path and detecting said x-rays with said x-ray image detector; and
   automatically electronically determining an artificial second x-ray image, which does not contain said x-ray structure, from said first x-ray image and from said x-ray attenuation.

6. A method as claimed in claim 1 comprising employing a movable x-ray source, as said x-ray source, and employing a movable x-ray image detector, as said x-ray image detector.

7. A method as claimed in claim 6 comprising:
   acquiring a series of x-ray images of said examination subject respectively at a plurality of different projection directions corresponding to different positions of said x-ray source and said x-ray image detector relative to each other;
   for each of said x-ray images in said series, automatically electronically determining the position of the x-ray source relative to said x-ray image detector; and
   electronically, reconstructing a 3D image of a volume of the examination subject from said series of x-ray images, using the determined positions of the x-ray source relative to the x-ray image detector.

8. A method as claimed in claim 7 comprising fixing said x-ray image detector in a fixed position relative to said examination subject, and panning said x-ray source through a predetermined azimuthal and elevation angle range relative to a surface normal of said x-ray image detector, to acquire said series of x-ray image.

9. A method as claimed in claim 7 comprising moving at least one of said movable x-ray source and said movable x-ray detector manually.

10. A method as claimed in claim 7 comprising moving at least one of said movable x-ray source and said movable x-ray detector automatically.

11. An x-ray system for determining a position of an x-ray source relative to an x-ray image detector in an x-ray imaging system, comprising:
    an x-ray source and an x-ray image detector;
    a reference structure introduceable into a beam path of x-rays between said x-ray source and said x-ray image detector, at a known position relative to the x-ray source, said x-ray image detector acquiring an x-ray image in which said reference structure is mapped; and
    a processing unit that automatically determines a position of the map of the reference structure in the x-ray image, and automatically determines a position of the reference structure relative to the x-ray image detector from the position of the map of the reference structure in the x-ray image, and automatically determines a position of the x-ray source relative to the x-ray image detector from the position of the reference structure relative to the x-ray image detector and the position of the reference structure relative to the x-ray source.

12. An x-ray system as claimed in claim 11 wherein said x-ray source has a beam exit aperture, and wherein said reference structure is a structured x-ray mask attached in front of said exit aperture of said x-ray source.

13. An x-ray system as claimed in claim 12 wherein said structured x-ray mask comprises a plurality of locally-differing plate thicknesses.

14. An x-ray system as claimed in claim 11 wherein said reference structure comprises an asymmetric cross having cross-arms of respectively different widths.

15. An x-ray system as claimed in claim 11 wherein said processing unit determines an x-ray attenuation caused by said reference structure in said beam path between said x-ray source and said x-ray image detector, and wherein said x-ray image is a first x-ray image and wherein said computer automatically determines an artificial second x-ray image, which does not contain said x-ray structure, from said first x-ray image and from said x-ray attenuation.

16. An x-ray system as claimed in claim 11 wherein said x-ray source is a movable x-ray source, and wherein said x-ray image detector is a movable x-ray image detector.

17. An x-ray system as claimed in claim 16 wherein said x-ray image detector acquires a series of x-ray images of said examination subject respectively at a plurality of different projection directions corresponding to different positions of said x-ray source and said x-ray image detector relative to each other, and wherein said processing unit, for each of said x-ray images in said series, automatically determines the position of the x-ray source relative to said x-ray image detector, and reconstructs a 3D image of a volume of the examination subject from said series of x-ray images, using the determined positions of the x-ray source relative to the x-ray image detector.

18. An x-ray system as claimed in claim 17 wherein said x-ray image detector is fixed in a fixed position relative to said examination subject, and said x-ray source is panned through a predetermined azimuthal and elevation angle range relative to a surface normal of said x-ray image detector, to acquire said series of x-ray image.

19. An x-ray system as claimed in claim 16 wherein at least one of said movable x-ray source and said movable x-ray detector is manually movable.

20. An x-ray system as claimed in claim 16 wherein at least one of said movable x-ray source and said movable x-ray detector is automatically movable.

* * * * *